United States Patent
Dawson

(10) Patent No.: US 9,239,347 B2
(45) Date of Patent: Jan. 19, 2016

(54) SIGNAL STABILIZATION IN A NON-RESISTIVE CONTACT SENSOR ASSEMBLY

(71) Applicant: RESCON LTD, Farnborough (GB)

(72) Inventor: Thomas Andrew Dawson, Aldershot (GB)

(73) Assignee: RESCON LTD, Farnborough (GB)

( * ) Notice: Subject to any disclaimer, the term of this patent is extended or adjusted under 35 U.S.C. 154(b) by 354 days.

(21) Appl. No.: 13/834,918

(22) Filed: Mar. 15, 2013

(65) Prior Publication Data

US 2014/0062508 A1    Mar. 6, 2014

Related U.S. Application Data

(60) Provisional application No. 61/695,986, filed on Aug. 31, 2012.

(51) Int. Cl.
| | |
|---|---|
| G01R 27/26 | (2006.01) |
| A61B 5/00 | (2006.01) |
| A61B 5/02 | (2006.01) |
| A61B 5/04 | (2006.01) |
| A61B 5/0408 | (2006.01) |
| A61B 5/0416 | (2006.01) |
| G01R 29/12 | (2006.01) |

(52) U.S. Cl.
CPC .......... *G01R 27/2605* (2013.01); *A61B 5/0408* (2013.01); *A61B 5/0416* (2013.01); *A61B 5/04085* (2013.01); *G01R 29/12* (2013.01)

(58) Field of Classification Search
CPC ............. A61N 1/36; A61N 1/37; A61B 5/04; A61B 5/0006; A61B 5/02; A61B 5/68; G01R 27/26

USPC ............ 324/126, 658, 686, 457, 663; 607/72, 607/119; 600/14, 300, 301, 372, 15, 179, 600/483, 513, 544, 546

See application file for complete search history.

(56) References Cited

U.S. PATENT DOCUMENTS

| | | | |
|---|---|---|---|
| 6,952,606 B2 | 10/2005 | Anderson et al. | |
| 2005/0054941 A1* | 3/2005 | Ting et al. | 600/529 |
| 2005/0275416 A1* | 12/2005 | Hervieux et al. | 324/663 |
| 2006/0041200 A1* | 2/2006 | Dotter et al. | 600/502 |
| 2008/0287770 A1* | 11/2008 | Kurzweil et al. | 600/388 |
| 2009/0254134 A1 | 10/2009 | Nikolov et al. | |
| 2010/0160737 A1 | 6/2010 | Schachar et al. | |
| 2011/0071412 A1* | 3/2011 | Kuo et al. | 600/509 |
| 2014/0062504 A1 | 3/2014 | Dawson | |
| 2014/0062505 A1 | 3/2014 | Dawson | |
| 2014/0125358 A1 | 5/2014 | Dawson et al. | |
| 2014/0152319 A1 | 6/2014 | Dawson et al. | |
| 2014/0218058 A1 | 8/2014 | Dawson et al. | |

OTHER PUBLICATIONS

Information Disclosure Statement (IDS) Letter Regarding Common Patent Application(s), dated Aug. 14, 2014.

* cited by examiner

*Primary Examiner* — Tung X Nguyen
*Assistant Examiner* — Neel Shah
(74) *Attorney, Agent, or Firm* — Tillman Wright, PLLC; Chad D. Tillman; Jeremy C. Doerre

(57) ABSTRACT

A non-resistive contact sensor assembly includes an electric field sensor device, including a dry electrode component for receiving an electrical signal from an object of interest and a signal processing component for processing the electrical signal, and a casing in which the signal processing component is surrounded or embedded. The processing component may include communications capabilities.

18 Claims, 13 Drawing Sheets

SIGNAL STABILIZATION IN A NON-RESISTIVE CONTACT SENSOR ASSEMBLY

CROSS-REFERENCE TO RELATED APPLICATIONS

The present application is a U.S. non-provisional patent application of, and claims priority under 35 U.S.C. §119(e) to, U.S. provisional patent application Ser. No. 61/695,986 to Dawson, filed Aug. 31, 2012 and entitled "SIGNAL STABILIZATION IN A NON-RESISTIVE CONTACT SENSOR ASSEMBLY," which '986 application is incorporated by reference herein in its entirety. Additionally, the entirety of each of the following, commonly-assigned U.S. patent applications, and any application publication thereof, is expressly incorporated herein by reference:

(a) U.S. provisional patent application Ser. No. 61/671,647 to Dawson, filed Jul. 13, 2012 and entitled "REDUCING MOVEMENT AND ELECTROSTATIC INTERFERENCE IN A NON-RESISTIVE CONTACT SENSOR ASSEMBLY;"

(b) U.S. provisional patent application Ser. No. 61/759,827 to Dawson, filed Feb. 1, 2013 and entitled "SIGNAL STABILIZATION IN A DIELECTRIC SENSOR ASSEMBLY;"

(c) U.S. non-provisional patent application Ser. No. 13/834,664, filed Mar. 15, 2013, and entitled, "REDUCING MOVEMENT AND ELECTROSTATIC INTERFERENCE IN A NON-RESISTIVE CONTACT SENSOR ASSEMBLY;" and (d) U.S. non-provisional patent application Ser. No. 13/835,762, filed Mar. 15, 2013, and entitled, "SIGNAL STABILIZATION IN A DIELECTRIC SENSOR ASSEMBLY."

STATEMENT REGARDING FEDERALLY SPONSORED RESEARCH OR DEVELOPMENT

This invention was made with government support under contract number W911NF-12-C-0004 awarded by DARPA. The government has certain rights in the invention.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

1. Field of the Present Invention

The present invention relates generally to electric field sensors, and, in particular, to signal stabilization in a non-contact resistive contact sensor assembly.

2. Background

Conventional electrodes act as a current transducers converting ionic currents into electronic ones so electrophysiological status can be assessed. The uses for this approach are many and broadly range from assessment of neural (EEG), cardiac (ECG), and skeletal (EMG) muscle activity.

This approach requires conductive contact with the source and has inherent problems. The first of these is the requirement of clean skin exposure. This requirement may compromise continuous usability due to the effects of environmental contaminants, both on the skin and in the atmosphere; extremes of temperature and their resulting general effect on skin due to physiological reactions such as "goose bumps" and excessive sweating as well as other phenomena; and potential reactions to conductive materials. The process of preparing skin and securing a good conductive contact can also decrease compliance, especially in if intended for continuous day to day use. Furthermore, during exercise, the physicality can result in electrodes being displaced. Other issues include shorting between electrodes, especially when placed in close proximity to each other, and charge transfer which has potential safety implications as well as the issue of the measurement process corrupting the signal.

The problems, outlined above, may be at least partially solved by the use of capacitive electrodes (non-resistive contact sensors) as they acquire signals through capacitive coupling, not requiring resistive contact with the source. They provide many benefits, including the fact that no electrical contact is required, and so no skin preparation or conducting pads are necessary and they can be readily moved or relocated to get an optimal signal. In addition, they can be miniaturized, they have very low power requirements, and they can be embodied as passive electric field sensors with the result that adjacent sensors do not interfere with each other.

The use of capacitive electrodes for electrophysiological monitoring is not a recent innovation, with Richardson describing it for acquisition of the cardiac signal in 1967[1]. This system was, however, flawed being prone to problems including poor signal to noise ratio, voltage drift, electrostatic discharge and parasitic capacitance. These are still problems with capacitive sensor technologies today. Many of those problems have been addressed, at least partially, but problems with signal stability interference still plague this technology. Signal stability interference is especially problematic during movement. Movement may lead to a variety of issues that may compromise continuous signal acquisition including contact electrification between the body surface and the sensor electrode; charge build-up on the body resulting in baseline shift and potential saturation if occurs too rapidly; and movement of the sensor relative to the body that can also lead to baseline shift and saturation (railing).

[1] *The insulated electrode: a pasteless electrocardiographic technique.* Richardson P C. Proc. Annu. Conf. on Engineering in Medicine and Biology 7:9-15 (1967)

When dry contact electrodes are placed in direct contact with a person, and particularly when they are moved, triboelectric effects (electrical charges created by sliding friction and pressure) are frequently generated. Triboelectric effects of this nature may cause contact electrification where static charges may be delivered to the pick-up electrode. This static charge can produce a near-direct current (DC) or very low frequency drift in the sensor that may interfere with the physiological alternating current (AC) signal that is being measured or may saturate the sensor causing railing, after which the sensor takes time to return to being able to produce a useful physiologically-relevant output. If the electrode moves relative to the body, it will also pick up a geoelectric displacement signal. That is, the effect of the body, an electrically active structure, moving through the geoelectric field, which is on the order of 100 $Vm^{-1}$, will cause relative polarization of the sensor that will displace the baseline and may cause the sensor to saturate. An additional source of interference is that of clothing moving on the body. As clothing moves on the body, charge separation can occur when materials that are separated on the triboelectric series donate or receive electrons from each other. After a material becomes charged it may discharge onto the surface where an electric potential is being measured, thereby interfering with signal acquisition.

Various issues can arise as a result of these various forms of interference. For example, issues may arise in the signal acquisition phase due to corruption of the signal from local electrical activity, in the signal referencing phase due to poor referencing of the signal to an appropriate earth, and during the transfer of the signal to processing units where the signal may be susceptible to interference. Thus, a need exists for devices, methods, and/or systems for reducing interference and stabilizing the signals being acquired and processed.

SUMMARY OF THE PRESENT INVENTION

Broadly defined, the present invention according to one aspect is a non-resistive contact sensor assembly, including: an electric field sensor device, including a dry electrode component for receiving an electrical signal from an object of interest and a signal processing component for processing the electrical signal; and a casing in which the signal processing component is surrounded or embedded.

In a feature of this aspect, the signal processing component includes an A/D converter for converting the electrical signal from the object of interest to a digitized signal.

In another feature of this aspect, the signal processing component is electrically shielded from the dry electrode component by an internal partition. In further features, the internal partition is provided in the form of a circuit board; the signal processing component is an A/D converter, and wherein the assembly further comprises at least one additional signal processing component, electrically shielded from the dry electrode component by the internal partition, for processing the output of the A/D converter; the assembly further includes an amplifier component that is distinct from the dry electrode component, and wherein the signal processing component is electrically shielded from the amplifier component by the internal partition; the internal partition is a structural extension of the casing; the signal processing component is a transmitter for transmitting a resulting digitized signal to another location (wirelessly and/or or over a data cable physically connected to the assembly); and/or the assembly further includes a circuit board on which the signal processing component is mounted, and wherein the circuit board is electrically shielded from the dry electrode component by the internal partition.

In another feature of this aspect, the casing is part of a housing for the assembly, and wherein the dry electrode component is exposed to the exterior of the housing. In a further feature, the casing is electrically isolated from the dry electrode component.

In another feature of this aspect, the dry electrode component is adapted to avoid resistive contact with a surface of the object of interest. In a further feature, the dry electrode component is adapted to avoid resistive contact with human skin.

In another feature of this aspect, the casing is adapted to made direct resistive contact with a surface of the object of interest. In a further feature, the dry electrode component is adapted to avoid resistive contact with human skin.

In another feature of this aspect, the assembly is in the form of a sensor head.

In another feature of this aspect, the casing is electrically grounded. In further features, the casing is electrically grounded via a ground connection to a power cable physically connected to the assembly; and/or the casing serves as a reference with regard to the electrical signal from the object of interest.

In another feature of this aspect, the casing is a conductive casing that acts as an electrical reference with regard to the electrical signal from the object of interest.

Broadly defined, the present invention according to another aspect is a non-resistive contact sensor assembly, including: an electric field sensor device, including a dry electrode component for receiving an electrical signal from an object of interest by capacitively coupling with the entity; a housing in which the signal processing component is surrounded or embedded; and an anode and a cathode, distinct from the dry electrode component, that together provide a stable surface field, thereby allowing more focused acquisition of the electrical signal from the object of interest.

In a feature of this aspect, the distinct anode and cathode are disposed in the housing with the dry electrode component.

In another feature of this aspect, the distinct anode is exterior to the housing.

In another feature of this aspect, the distinct cathode is exterior to the housing.

In another feature of this aspect, the stable surface field is subtracted computationally during post-acquisition processing of the electrical signal from the object of interest.

In another feature of this aspect, the assembly is in the form of a sensor head.

Broadly defined, the present invention according to another aspect is a non-resistive contact sensor assembly, including: an electric field sensor device, including a dry electrode component for receiving an electrical signal from an object of interest by capacitively coupling with the entity; a cover in which the signal processing component is surrounded or embedded; and a biasing structure, disposed on the outside of the cover, that are adapted to press the dry electrode component against a surface of the object interest when biased by an external structure.

In a feature of this aspect, the biasing structure is a spring. In a further feature, the spring is a mechanical spring with a polymeric, metallic, and/or fiber material construction.

In another feature of this aspect, the biasing structure is comprised of compressive material. In a further feature, the compressive material is selected from a group comprising rubber, felt, elastomeric, polymeric, closed cell foam and analogues.

In another feature of this aspect, the assembly is arranged in a helmet that comprises the external structure.

In another feature of this aspect, the assembly is arranged beneath a belt that comprises the external structure.

In another feature of this aspect, the assembly is arranged beneath jewelry that comprises the external structure In another feature of this aspect, the assembly is arranged beneath an article of clothing that comprises the external structure.

In another feature of this aspect, the assembly is arranged in a piece of furniture that comprises the external structure.

In another feature of this aspect, the assembly is arranged in a vehicle seat that comprises the external structure. In features of this aspect, the vehicle seat is an automobile seat, an airplane seat, a rail locomotive seat, or a wheelchair seat.

In another feature of this aspect, the assembly is in the form of a sensor head.

Broadly defined, the present invention according to another aspect is a non-resistive contact sensor assembly as shown and described.

Broadly defined, the present invention according to another aspect is a sensor head for a non-resistive contact sensor assembly as shown and described.

Broadly defined, the present invention according to another aspect is a method of reducing movement in a non-resistive contact sensor assembly, as shown and described.

Broadly defined, the present invention according to another aspect is a method of signal stabilization in a non-resistive contact sensor assembly, as shown and described.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
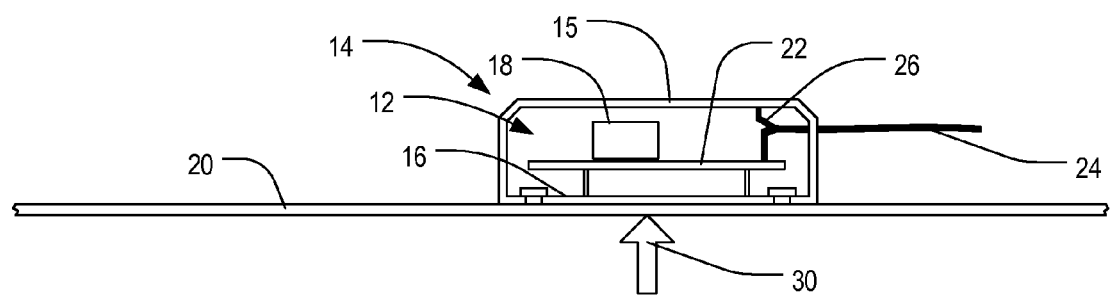
FIG. 1 is a schematic diagram of a non-resistive contact sensor assembly in accordance with a first preferred embodiment of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

In various aspects, the present invention relates to methods of attenuating or eliminating unwanted movement or electrostatic interference on signals acquired via non-resistive contact sensors from various entities, both biological and other. Such sensors may be used by themselves, or may be used in combination with other sensors. The sensor data is utilized for detecting properties of the entities.

For biological entities, the invention utilizes an electric field sensor or sensors for the measurement of the structural and functional characteristics of organs and other structures where the electric field sensor does not have resistive contact with the organism, conferring multiple advantages. In various aspects, the present invention relates to sensors, sensor housings, fastenings and sensor systems including devices and installations for assemblies for detecting structural and functional signatures associated with electric potentials that may detect a displacement signature within the geomagnetic field, and/or specific components and/or structures that are a component of that entity or entities. There is preferably no resistive contact between the entity and the signal transduction component of the electric field sensor or sensors. Other sensor types may be added in to provide further information, such as for the identification and elimination or attenuation of unwanted electrostatic or movement signal associated with the recording of non-resistive contact electric fields from that entity, in whatever state, such as during active or passive movement.

In particular, the present invention, in various aspects, relates to novel methods and apparatuses for stabilizing the target signal when using an electric field sensor or sensors of the type that does not have resistive contact with the entity, generally an organism, which is being monitored. In various aspects, the invention relates to combinations and permutations of: applying an electric field to electrically stabilize the sensor zone; the use of a conductive casing to act as a reference for the signal that is being acquired; the use of an analog to digital converter in the sensor head to digitally fix the signal; the use of a barrier (guard or shield) between the analog to digital converter to mitigate signal corruption the converter; a logic board to process the signal in the sensor head; a compressive material, spring, or another component in tension against another fixed structure, such as a helmet, to hold the referencing component and/or the electrode firmly on the surface of the entity being measured; a cable or wireless transmitter to transmit the digitized signal; and/or a resistive contact electrode that may be incorporated into the reference casing or used as a separate component to add signal acquisition resilience.

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

FIG. 1 is a schematic diagram of a non-resistive contact sensor assembly 10, or at least a sensor head thereof, in accordance with a first preferred embodiment of the present invention. The sensor assembly 10 includes a electric field sensor device 12, an analog-to-digital (A/D) converter 18, an internal partition 22, a power and data cable 24, and a housing 14. The sensor device 12 is at least partially surrounded by, or embedded in, the housing 14, at least portions of which may be made of anti-triboelectric material. In various respects, the sensor assembly 10 and sensor device 12 may have one or more characteristics described in the '664 application.

The sensor device 12 includes a dry electrode component 16 that is exposed to the exterior of the housing 14 and is arranged to avoid resistive contact with the skin or other surface 20 on which the sensor assembly 10 is placed. However, the sensor electrode 16 is capacitively coupled to the skin or other surface 20 of the entity being analyzed and may be in physical contact with the surface 20 so long as resistive contact is avoided. In at least some embodiments, physical contact is avoided so as to avoid resistive contact.

The housing 14 includes a conductive casing (shielding) 15 that makes direct resistive contact with the skin or other surface 20 on which the sensor assembly 10 is placed but is electrically isolated from the electrode 16. The casing 15, which as noted makes resistive contact with the surface 20, is grounded by a ground connection 26 to the power and data cable 24 to the unit 10. The casing 15 may thus serve as a reference with regard to a target signal 30 from the object of interest.

After the signal from the electrode 16 is amplified, it is converted to a digital signal by the A/D converter 18. Notably, the A/D conversion is carried out within the confines of the sensor casing 15, and in at least some embodiments, the amplification is likewise carried out within the confines of the sensor casing 15. The A/D converter 18 is also shielded from the electrode 16 itself by the internal partition 22, which is designed to provide an electrical field barrier against the electrode 16 and the amplification thereof. In this regard, it will be appreciated that in at least some embodiments, amplification likewise takes place on the opposite side of the partition 22 from the A/D converter 18. Advantageously, the shielding offered by the partition 22 helps to prevent the A/D converter 18 from being affected by interference caused by various electrical effects. The partition 22 may take any of a variety of forms, including as a structural extension of the casing 15.

Other processing components may also be shielded from the electrode 16 and amplification by the partition 22. In at least some embodiments, the partition 22 is provided in the form of a circuit board, and the other processing components may be disposed on the circuit board 22. In other embodiments, a circuit board is provided, but is separate from the partition 22 and is shielded by the partition 22 from the electrode 16 and amplification. Furthermore, in addition to, or included within, the other processing components, a transmitter (not shown) may be provided, within the casing 15 and shielded by the circuit board or other partition 22, for transmitting a resulting digitized signal to another location. Such transmission may occur wirelessly or over the power and data cable 24, and is similar protected from interference by the casing 15 and the circuit board or other partition 22.

Figure 2:
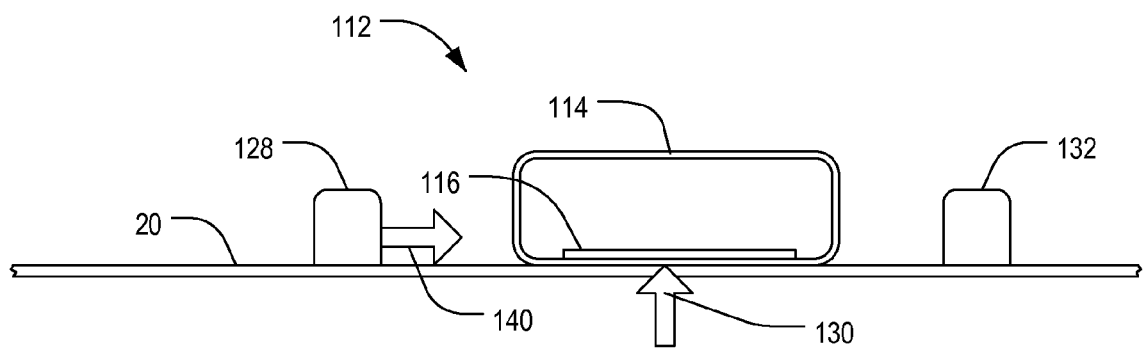
FIG. 2 is a schematic diagram of a non-resistive contact sensor assembly in accordance with another preferred embodiment of the present invention.

FIG. 2 is a schematic diagram of a non-resistive contact sensor assembly 110, or at least a sensor head thereof, in accordance with another preferred embodiment of the present invention. The sensor assembly 110 includes an electric field sensor device 112 at least partially surrounded by, or embedded in, a cover 114, which may be of anti-triboelectric material. In various respects, the sensor assembly 110 and sensor device 112 may have one or more characteristics described in the '664 application. Furthermore, the sensor device may incorporate characteristics of the sensor device 12 of FIG. 1, described previously. The sensor device 112 of FIG. 2 includes a non-resistive contact electrode component 116, an anode 128, and a cathode 132. In at least some embodiments, the non-resistive contact electrode component 116 is interior to the cover 114, but this is not required. Furthermore, although in the illustrated embodiment the anode 128 and cathode 132 are exterior to the cover 114, it will be appreciated that in some embodiments, it may be possible to locate the anode 128 and cathode 132 interior to the cover 114.

An electric field 140 is produced by the anode 128 and cathode 132 to stabilize the electric potential, and particularly the surface electric potential, around the sensor assembly 110. This, in turn, allows more focused acquisition of the target field (signal) 130 being produced by the entity.

In FIG. 2, the sensor assembly 110 is shown making contact with the surface 20 of the entity being measured or analyzed. The electrode 116 capacitively couples to the entity to measure the target signal 130. The anode 128 produces an electron flow 140 toward the cathode 132, thereby providing a stable surface field. This field can be subtracted computationally as needed during post-signal acquisition processing.

Figure 3:
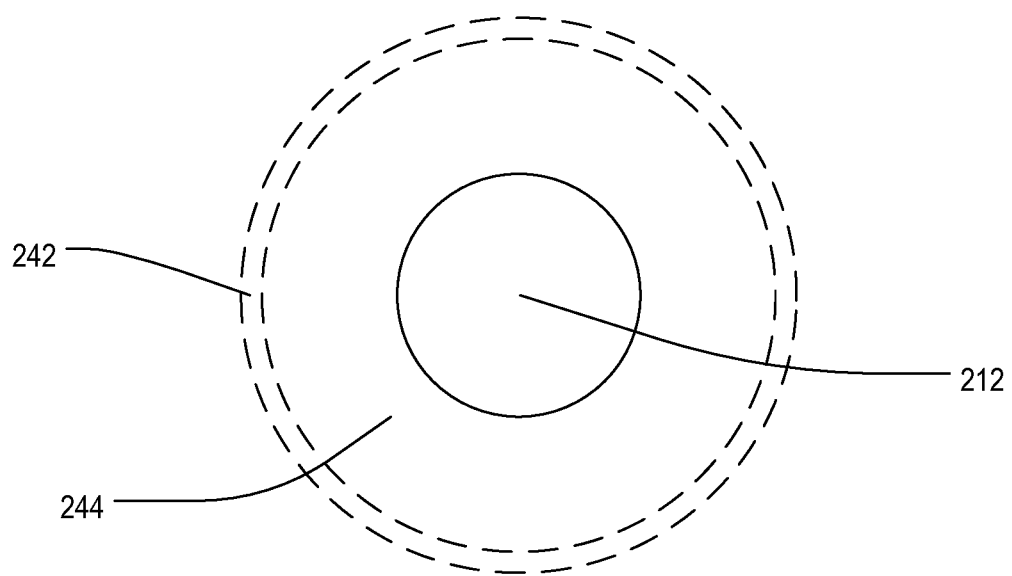
FIG. 3 is a schematic diagram of a hybrid sensor assembly in accordance with another preferred embodiment of the present invention.

FIG. 3 is a schematic diagram of a hybrid sensor assembly 210, or at least a sensor head thereof, in accordance with another preferred embodiment of the present invention. In this sensor assembly 210, two regions 242,244 surround a non-resistive contact electric field sensor device 212, including a dry electrode component (not separately shown). The inner region 244 could include a triboelectrically neutral or relatively neutral material, such as but not limited to cotton. One purpose in using such material is to avoid the buildup of electrostatic or other charges, because the material will be at least relatively resistant to, if not able to avoid altogether, accepting or donating electrons. The outer region 242 includes a conductive material and may include fastening/elastic/compressive materials. In various respects, the sensor assembly 210 and its components may have one or more characteristics described in the '664 application.

The sensor assembly 210 is used in conjunction with a conventional resistive contact electrometer to provide two interrogation routes of the electrical activity of the entity being measured, thereby enhancing the robustness of the overall system. At the periphery of the sensor assembly 210, the outer region of conductive material 242 makes resistive contact with the surface of entity whose signal is being measured or analyzed, thereby serving as the conductive portion of an electrode component of an electrometer used in a traditional ECG or other electrophysiological detection system. Meanwhile, the non-resistive contact electric field sensor device 212 operates as described herein and/or as described in the '664 application. Thus, two routes are provided for signal acquisition for an ECG system, thereby providing robustness to the overall system. In various versions of such an embodiment, the electrode component may be active or passive. Furthermore, it will be appreciated that such a sensor assembly 210 may be used with other devices as well, such as galvanometers and the like.

Figure 4A:
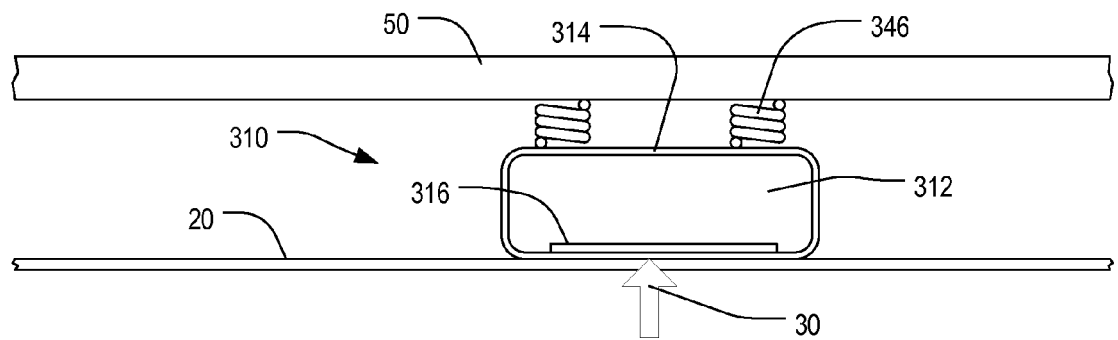
FIG. 4A is a schematic diagram of a non-resistive contact sensor assembly in accordance with another preferred embodiment of the present invention.

FIG. 4A is a schematic diagram of a non-resistive contact sensor assembly 310, or at least a sensor head thereof, in accordance with another preferred embodiment of the present invention. The sensor assembly 310 includes an electric field sensor device 312 at least partially surrounded by, or embedded in, a cover 314, which may be of anti-triboelectric material. In various respects, the sensor assembly 310 and sensor device 312 may have one or more characteristics described in the '664 application. Furthermore, the sensor device may incorporate characteristics of the other sensor devices described herein. The sensor device 312 of FIG. 4A includes a dry electrode component 316 that is interior to the cover 314. The sensor assembly 310 may also include one or more springs 346 disposed in locations that, when biased by an external structure 50, tend to push the sensor assembly 310 against the surface 20 of an object to which the sensor assembly 310 is being applied. This force tends to hold the sensor assembly 310 in place on the object surface 20, reducing triboelectric effects and the like that would otherwise be caused by relative movement of the sensor assembly 310. This, in turn, makes accurate acquisition and processing of the target signal 30. Various types may be suitable for use as the springs 346 of the present invention.

Figure 4B:
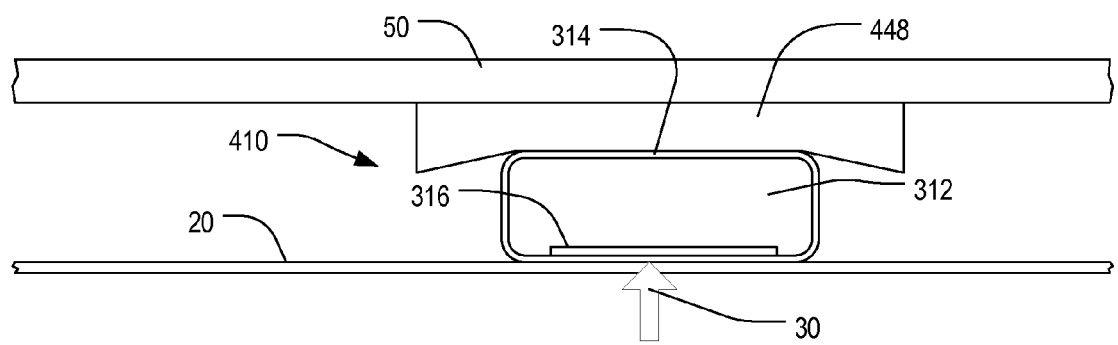
FIG. 4B is a schematic diagram of a non-resistive contact sensor assembly in accordance with another preferred embodiment of the present invention.

FIG. 4B is a schematic diagram of a non-resistive contact sensor assembly 410, or at least a sensor head thereof, in accordance with another preferred embodiment of the present invention. The sensor assembly 410 is similar in many respects to the sensor assembly 310 of FIG. 4A and includes an electric field sensor device 312 at least partially surrounded by, or embedded in, a cover 314, which may be of anti-triboelectric material. In various respects, the sensor assembly 310 and sensor device 312 may have one or more characteristics described in the '664 application. Furthermore, the sensor device may incorporate characteristics of the other sensor devices described herein. The sensor device 312 of FIG. 4B includes a dry electrode component 316 that is interior to the cover 314. The sensor assembly 410 also includes compressive material 348 disposed in a location or locations that, when biased by an external structure 50, tend to push the sensor assembly 410 against the surface 20 of an object to which the sensor assembly 410 is being applied. This force tends to hold the sensor assembly 410 in place on the object surface 20, reducing triboelectric effects and the like that would otherwise be caused by relative movement of the sensor assembly 410. This, in turn, makes accurate acquisition and processing of the target signal 30. Materials suitable for use with the present invention as a compressive material 348 may include rubber, felt, elastomeric, polymeric, closed cell foam and analogues, mechanical springs made out of polymers, metals, fibers, or any other material now known or hereafter developed that performs the function in an equivalent manner.

It will be appreciated that the external structure 50 that biases the sensor assemblies 310,410 of FIGS. 4A and 4B against the object surface 20 may be a portion of a helmet, belt, article of clothing, furniture, vehicle seating, or the like. With regard to vehicle seating, it will be appreciated that such seating could include seating for automobiles (including trucks), boats and other watercraft, rail locomotives, airplanes, motorized and non-motorized wheelchairs, and other vehicles.

A further embodiment is to use multiple sensors in an array so that if one or more signals is compromised by interference or otherwise with the sensor/s or its/their data acquisition then other sensors within the array can be used to gain a useful signal.

Figure 5A:
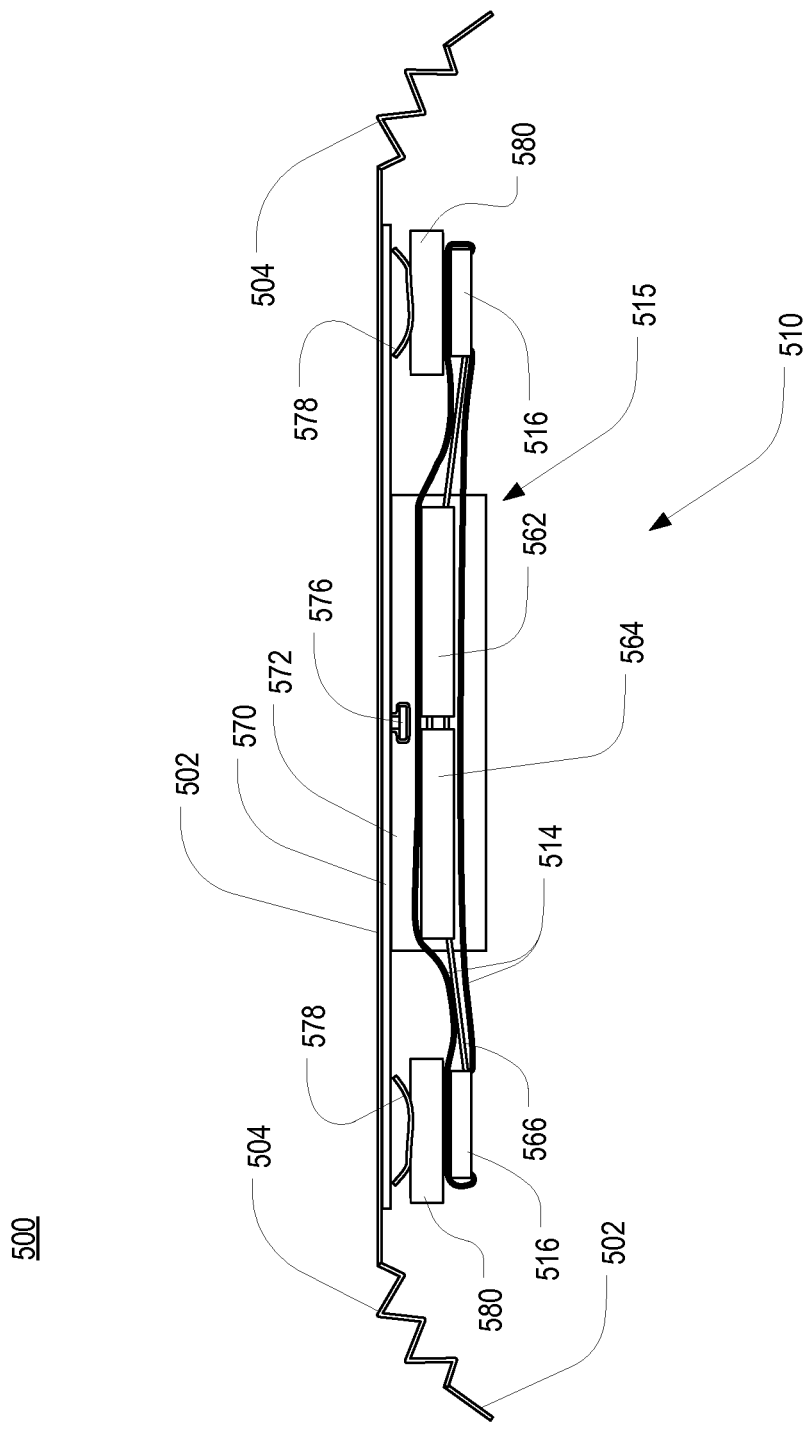
FIG. 5A is a fragmentary, partially schematic top view of a portion of a wearable sensor belt in accordance with one or more preferred embodiments of the present invention.
Figure 5B:
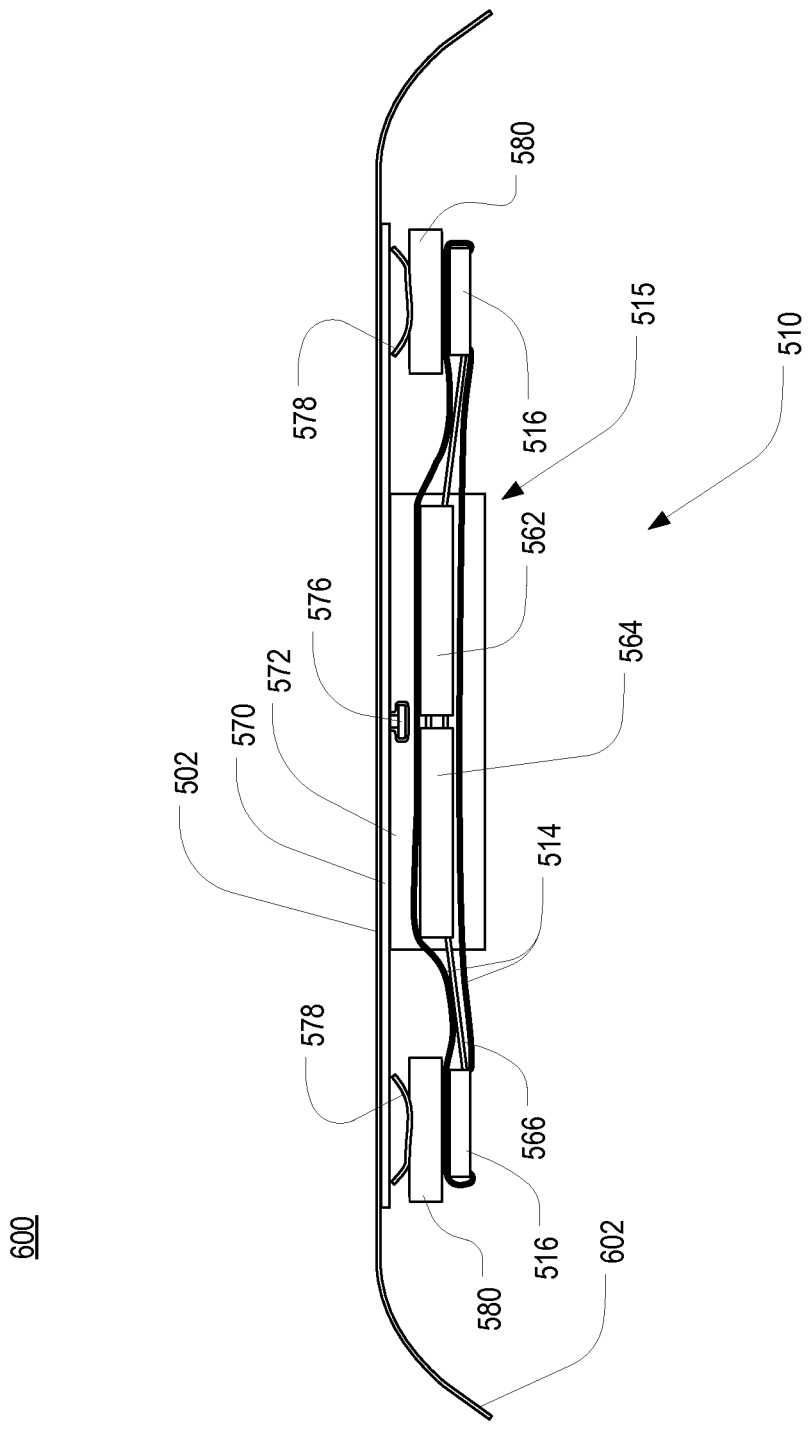
FIG. 5B is a fragmentary, partially schematic top view of a portion of another wearable sensor belt in accordance with one or more preferred embodiments of the present invention.

FIG. 5A is a fragmentary, partially schematic top view of a portion of a wearable sensor belt 500 in accordance with one or more preferred embodiments of the present invention. As shown therein, the wearable sensor belt 500 includes a sensor assembly 510 mounted on a tensioning belt 502. The tensioning belt 502 that is sized to facilitate the belt 500 being fastened around a portion 20 of a human body (shown in FIG. 8), such as a thoracic region (chest, upper back, or the like), head, arm, leg, or the like. The tensioning belt 502 preferably includes at least one elasticated section to assist in maintaining the sensor assembly snugly against the region 20 of the body being monitored. In addition to the elasticated section, the belt 502 may include one or more tensioning devices 504 disposed in the vicinity of the sensor assembly 510 in order to help provide additional biasing force to hold the sensor assembly 510 against the body 20. However, in some embodiments, such as that shown in FIG. 5B, the tensioning devices are omitted. Furthermore, the belt 502 may include a buckle, hook and loop fasteners (VELCRO®), or the like (not shown) in order to provide a better overall fit, provide greater biasing force against the sensor assembly 510, position the sensor assembly 510 better, or the like.

Figure 6:
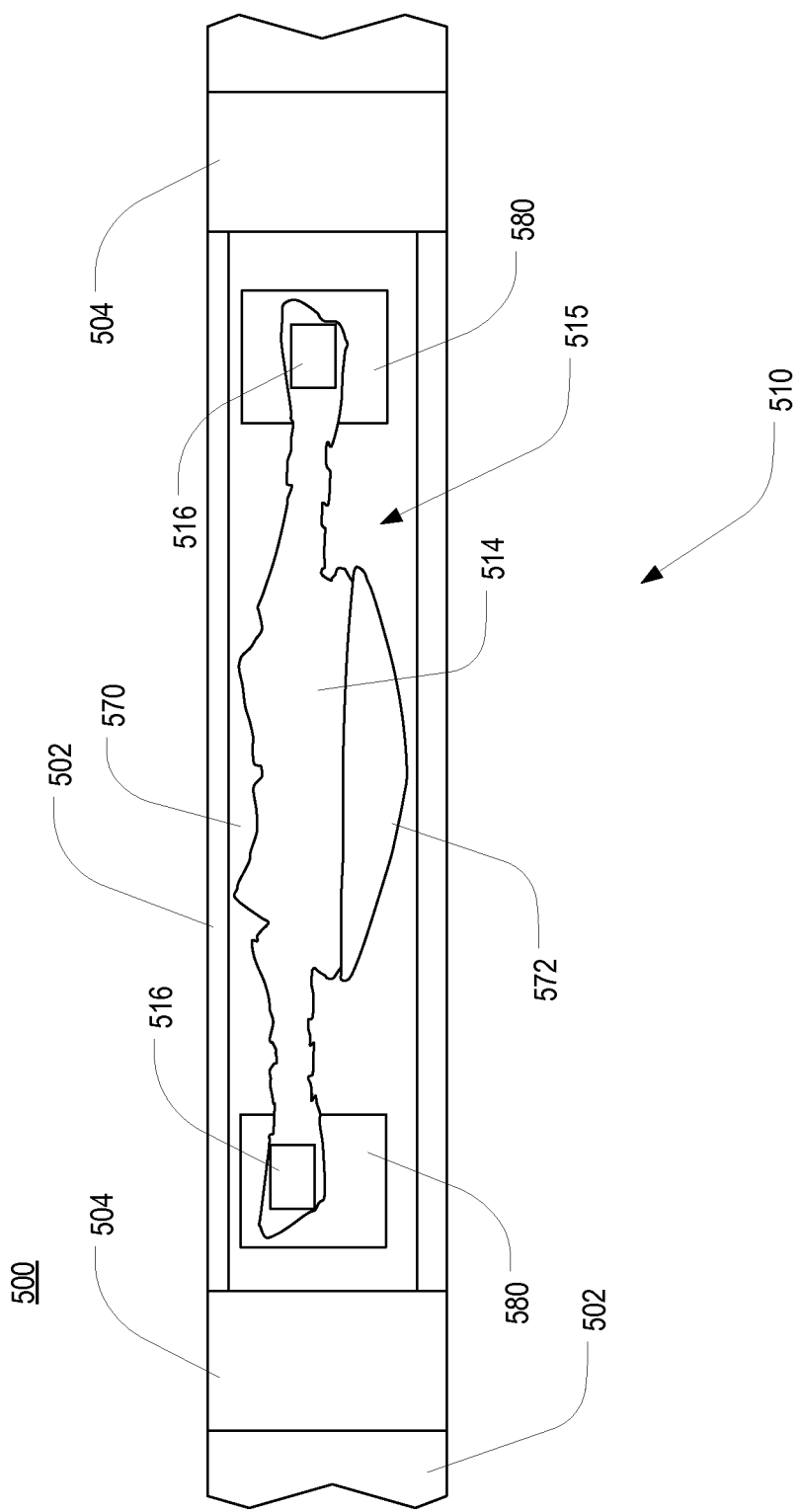
FIG. 6 is a fragmentary, partially schematic front view of the wearable sensor belt of FIG. 5A.

FIG. 6 is a fragmentary, partially schematic front view of the wearable sensor belt 500 of FIG. 5A. With reference to FIGS. 5A and 6, the sensor assembly 510 includes a plurality of electrodes 516 that are contained within, but exposed to the exterior of, a sleeve 514 that is resistant to triboelectric charging with human skin 20. In at least some embodiments, the sleeve 514 is made from neoprene. Also contained within the sleeve are one or more processing and communications components 562, one or more batteries 564, and various electrical connections 566. In at least some embodiments, the processing and communications 562 and most or all of the electrical connections 566 are provided in the form of a printed circuit board. The processing and communications components 562 preferably include wireless communication capabilities such as those provided via BLUETOOTH®, ZIGBEE®, or the like. The electrodes 516, processing and communications components 562, battery or batteries 564, electrical connections 566, and surrounding sleeve 514 together define a sensor casing 515.

Figure 7:
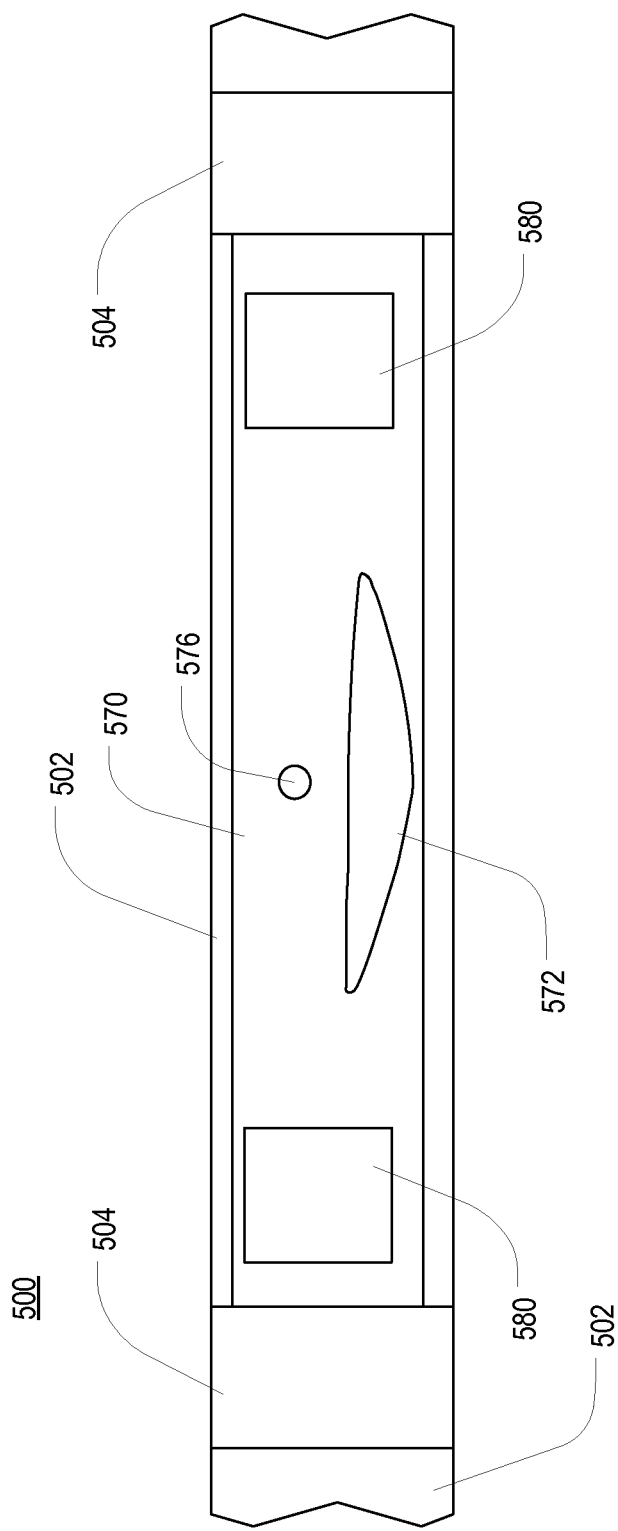
FIG. 7 is a fragmentary, partially schematic front view of the wearable sensor belt of FIG. 6, shown with the sensor casing removed.

The sensor assembly also includes a support wall 570 on which some or all of the various other components are carried. In some embodiments, a shelf 572 extends from the support wall 570 and provides support for the sensor casing 515. In some embodiments, a flange attachment 576 extends from the support wall 570 and mates with a corresponding groove, recess, or the like in the sensor casing 515. In this regard, FIG. 7 is a fragmentary, partially schematic front view of the wearable sensor belt 500 of FIG. 6, shown with the sensor casing 515 removed, thereby revealing the flange attachment 576. In some embodiments, including the one illustrated herein, both are provided. The support wall 570 may, for example, be constructed from a semi-rigid material such as polycarbonate. The shelf 572 likewise may, for example, be constructed from a semi-rigid structure, which may or may not be of the same material as that used for the support wall 570. Materials suitable for use in the support wall 570 and/or shelf 572 include plastics, such as polycarbonate; synthetic fibers, such as KEVLAR®; composites; layered composites; and the like. One possible exemplary construction may include carbon Kevlar with other materials such as cotton or polycarbonate layered in between.

In order to help ensure that the electrodes 516 themselves remain pressed against the skin surface 20 to which they are being applied, one or more biasing structures may be provided so as to transfer the force applied by the tensioning belt 502 to the electrodes 516. Such biasing structures may include a spring 578, a solid body 580 of a compressive material, or the like. Materials suitable for use in such a body 580 include neoprene closed cell foam, neoprene, and the like. As shown in FIG. 5A, two or more such structures 578,580 may be utilized in combination with each other.

Figure 8:
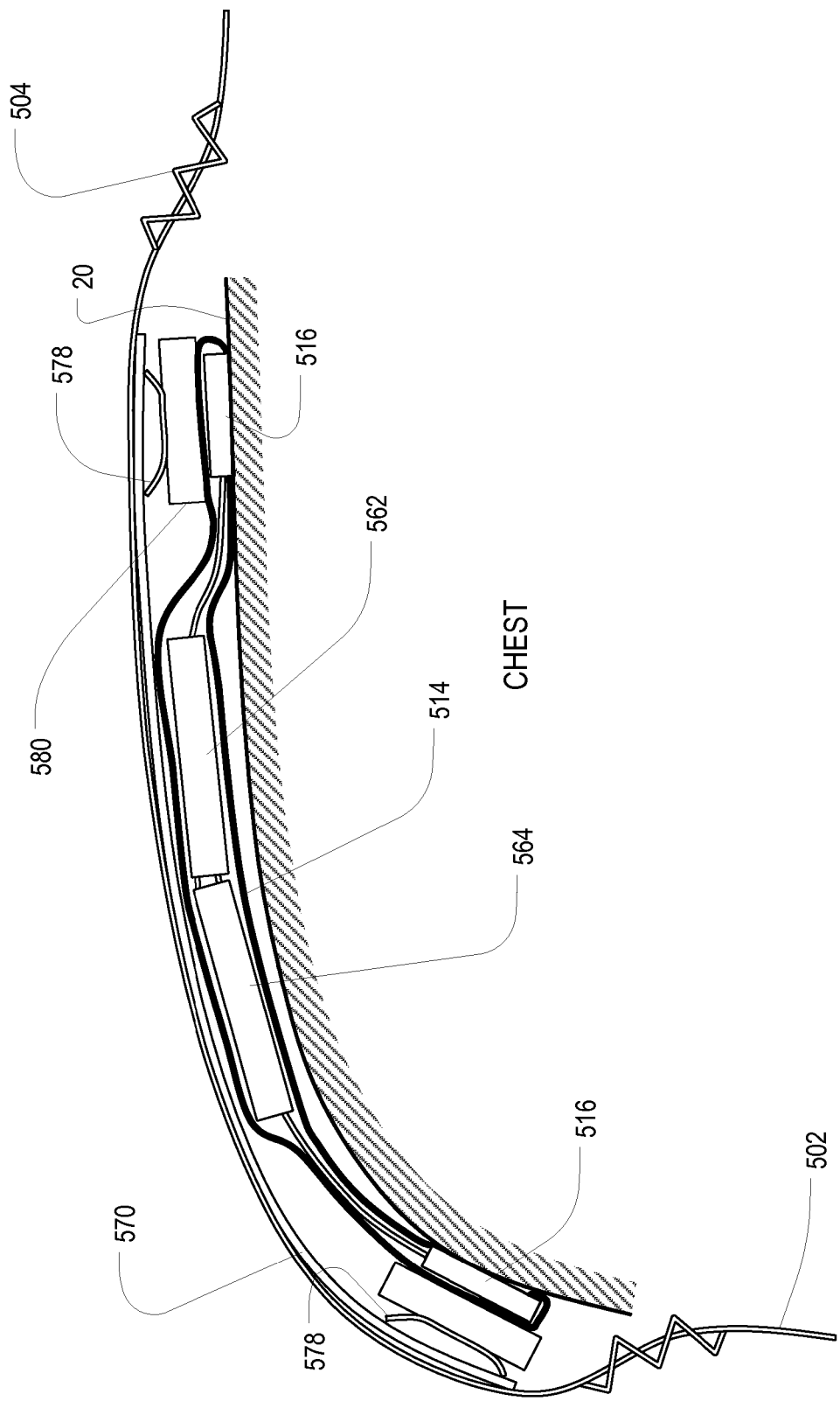
FIG. 8 is a fragmentary, partially schematic top view of the portion of the wearable sensor belt of FIG. 5A, shown in use against the chest of a human.

In use, the wearable sensor belt 500 is attached around the body part with the electrodes against or adjacent the skin 20. FIG. 8 is a fragmentary, partially schematic top view of the portion of the wearable sensor belt 500 of FIG. 5A, shown in use against the chest of a human. As shown therein, the belt 502 has been tightened against the chest. The tensioning devices 504 assist in making sure that the electrodes 516 are held against the skin 20, as are the springs 578 and compressible bodies 580. The sensor assembly 510 is thus positioned reliably against the skin surface 20, with the electrodes 516 remaining in contact even during vigorous activity by the wearer.

Figure 9:
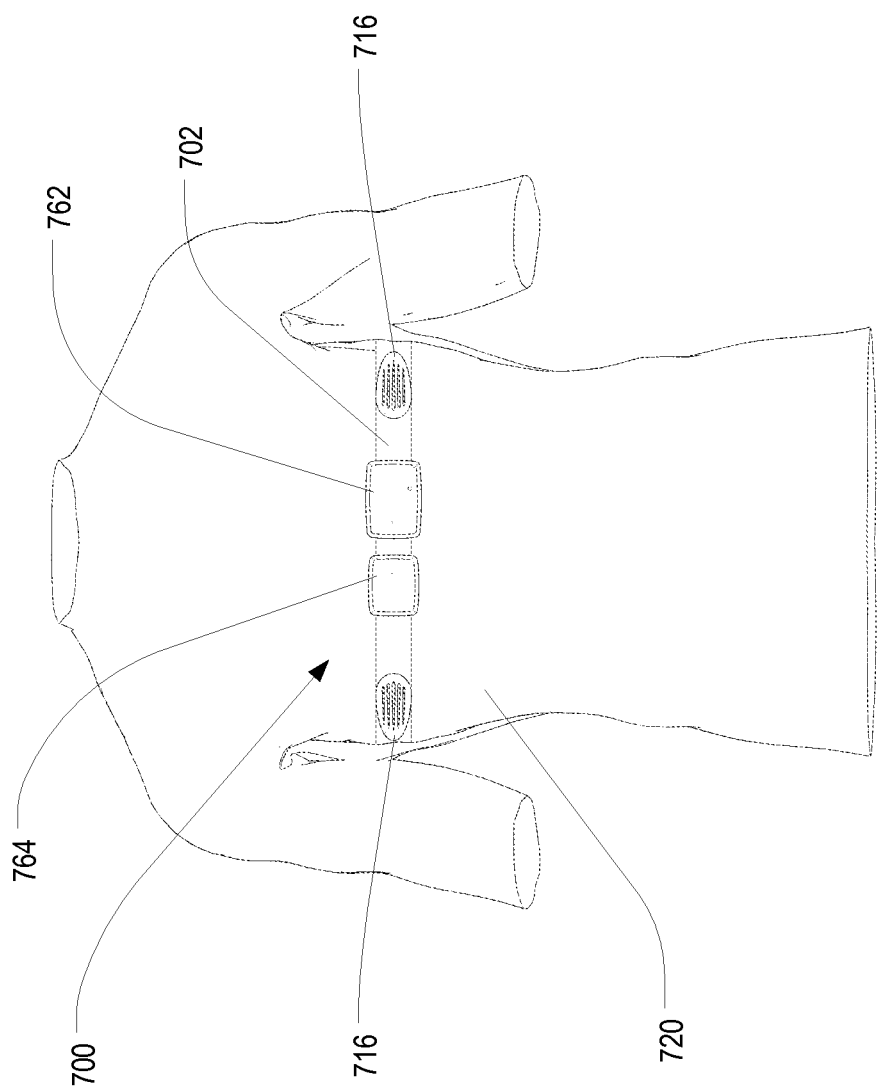
FIG. 9 is a front perspective view of a an exemplary wearable sensor belt attached around the chest of a human wearer in accordance with one or preferred embodiments of the present invention.
Figure 10:
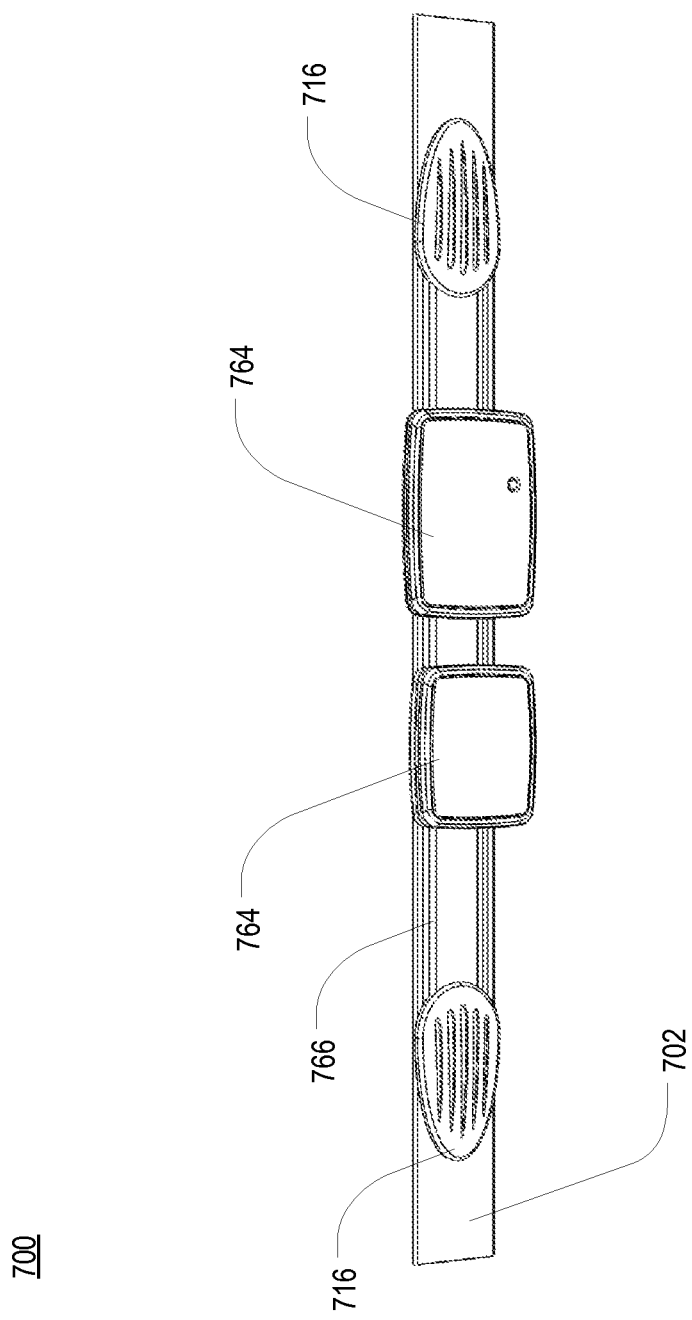
FIG. 10 is a fragmentary front perspective view of the wearable sensor belt of FIG. 9.

FIG. 9 is a front perspective view of a an exemplary wearable sensor belt 700 attached around the chest 720 of a human wearer in accordance with one or preferred embodiments of the present invention, and FIG. 10 is a fragmentary front perspective view of the wearable sensor belt 700 of FIG. 9. As shown therein, the wearable sensor belt 700 includes a sensor assembly mounted on a tensioning belt 702. In at least some embodiments, the tensioning belt 702 may have some or all of the characteristics described with regard to the tensioning belt of FIG. 5A. The sensor assembly includes a pair of electrode assemblies 716, a processing and communications component assembly 762, and a battery assembly 764. Each electrode assembly 716 includes at least one electrode having characteristics similar to those of electrodes described elsewhere herein, including the electrodes 516 of FIG. 5A. Likewise, the processing and communications component assembly 762 includes processing and communications components having characteristics similar to those described elsewhere herein, including those of the processing and communications components 562 of FIG. 5A, and the battery assembly 764 may include a battery like the battery 564 of FIG. 5A. In at least some embodiments, the processing and communications components, battery, and electrodes are connected to one another via ribbon wiring 766. One or more of the communications component assembly 762, the battery assembly 764, the electrode assemblies 716, and/or the ribbon wiring 766 may be encased in a triboelectric charging-resistant case or sleeve, including that described with respect to the wearable sensor belt 500 of FIG. 5A.

Figure 11:
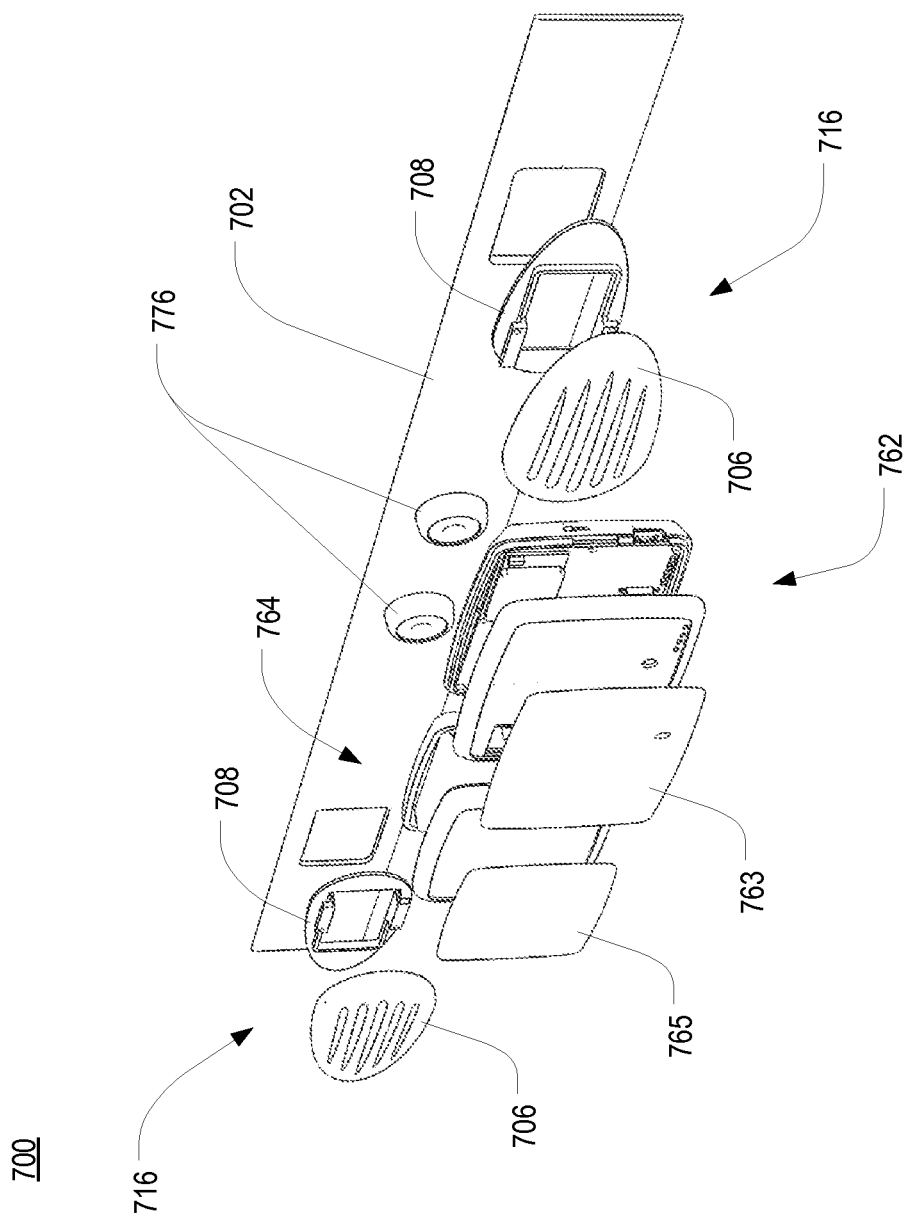
FIG. 11 is an exploded fragmentary front perspective view of the wearable sensor belt of FIG. 10.
Figure 12:
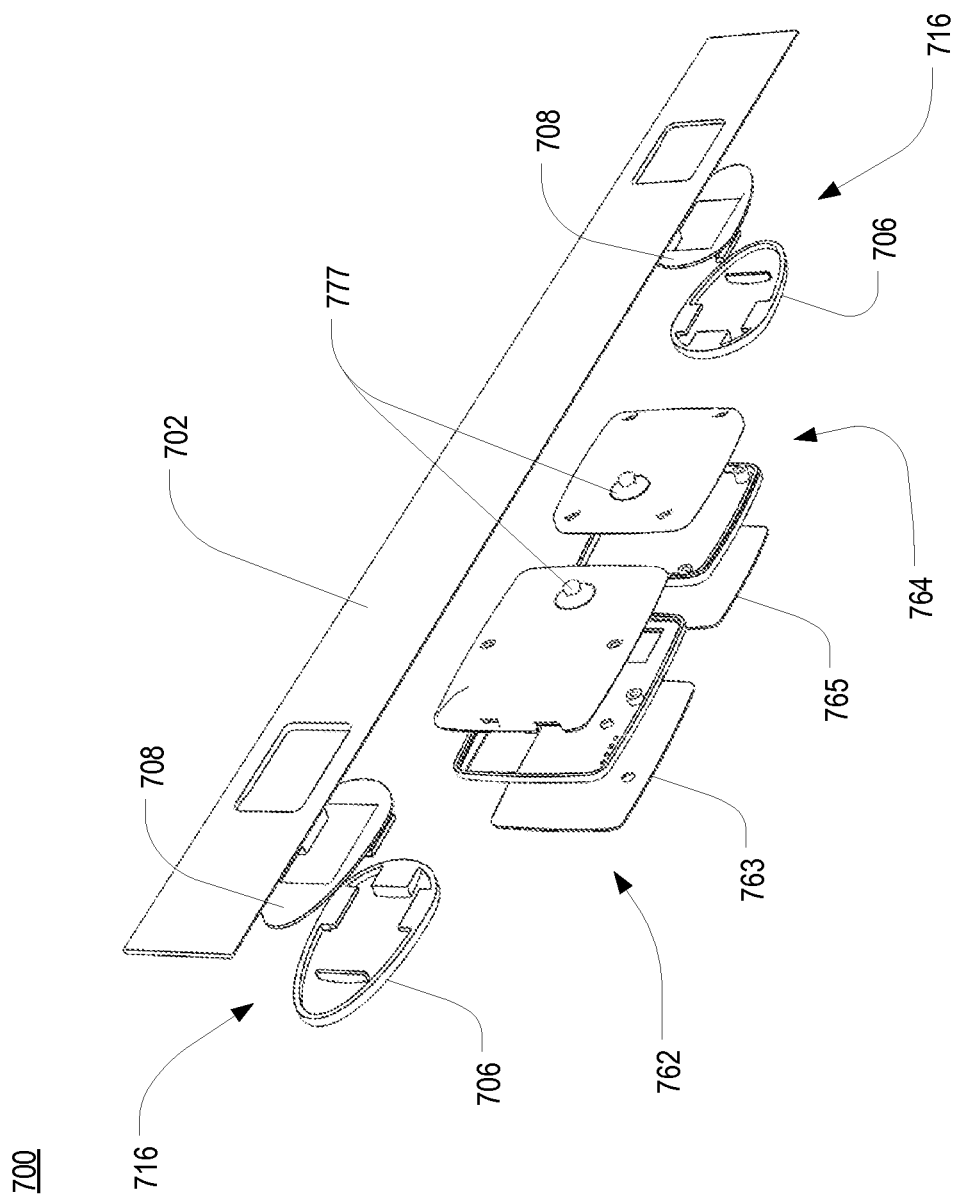
FIG. 12 is an exploded fragmentary rear perspective view of the wearable sensor belt of FIG. 10.

FIG. 11 is an exploded fragmentary front perspective view of the wearable sensor belt 700 of FIG. 10, and FIG. 12 is an exploded fragmentary rear perspective view of the wearable sensor belt 700 of FIG. 10. As shown therein, each electrode assembly 716 includes a clip 708 to fasten the main body 706 of the electrode to the belt 702. Furthermore, the housing components 763,765 of the processing/communications assembly 762 and battery assembly 764, respectively, may be fastened to the belt 702 via a snap assembly, wherein a button 776 for each is disposed on the belt 702, and a corresponding prong 777 is disposed on the back of each set of respective housing components 763,765.

Various advantages may be achieved using one or more of the foregoing embodiments of the present invention. The robustness of the measurement of the electrical signature of an entity or sub-component of that entity may be increased. A signal being measured or analyzed may be protected closer to the source, thereby protecting it from corruption. The stability of the signal may be enhanced. The signal-to-noise ratio for an electric field sensor may be enhanced. The effect of electrostatic charge interference with an electric field sensor may be minimizes or eliminated entirely. The use of electric field sensors during exercise and daily activities may be increased, as can the usability of electric field sensors with different types of clothing and when clothing is moving due to exercise or external forces (like wind). Similarly, the usability of electric field sensors may be increased when there is external contact that would otherwise knock the sensor loose or that would result in charge transfer to the entity being measured or analyzed. Conversely, the likelihoods of contact electrification, sensor DC drift, and sensor saturation may all be decreased.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A non-resistive contact sensor assembly, comprising:
    a dry electrode component for receiving an electrical signal from an object of interest;
    a signal processing component for processing the electrical signal, wherein:
        the signal processing component includes an A/D converter that converts the electrical signal from the object of interest to a digitized signal, and
        the dry electrode component and signal processing component together define an electric field sensor device; and
    a casing in which the signal processing component is surrounded or embedded;
    wherein the casing is part of a housing for the assembly, and wherein the dry electrode component is exposed to the exterior of the housing;
    wherein the casing is electrically isolated from the dry electrode component; and
    wherein the casing is electrically grounded via a ground connection to a power cable physically connected to the assembly.

2. The non-resistive contact sensor assembly of claim 1, wherein the signal processing component further includes a bandwidth filter that filters the electrical signal from the object of interest prior to being converted to a digitized signal by the A/D converter for converting the electrical signal from the object of interest to a digitized signal.

3. The non-resistive contact sensor assembly of claim 1, wherein the signal processing component, including the A/D converter, is electrically shielded from the dry electrode component by an internal partition.

4. The non-resistive contact sensor assembly of claim 3, wherein the internal partition is provided in the form of a circuit board.

5. The non-resistive contact sensor assembly of claim 3, wherein the signal processing component is an A/D converter, and wherein the assembly further comprises at least one additional signal processing component, electrically shielded from the dry electrode component by the internal partition, for processing the output of the A/D converter.

6. The non-resistive contact sensor assembly of claim 3, further comprising an amplifier component that is distinct from the dry electrode component, and wherein the signal processing component is electrically shielded from the amplifier component by the internal partition.

7. The non-resistive contact sensor assembly of claim 3, wherein the internal partition is a structural extension of the casing.

8. The non-resistive contact sensor assembly of claim 3, wherein the signal processing component is a transmitter for transmitting a resulting digitized signal to another location.

9. The non-resistive contact sensor assembly of claim 8, wherein the transmitting occurs wirelessly.

10. The non-resistive contact sensor assembly of claim 8, wherein the transmitting occurs over a data cable physically connected to the assembly.

11. The non-resistive contact sensor assembly of claim 3, further comprising a circuit board on which the signal processing component is mounted, and wherein the circuit board is electrically shielded from the dry electrode component by the internal partition.

12. The non-resistive contact sensor assembly of claim 1, wherein the dry electrode component is adapted to avoid resistive contact with a surface of the object of interest.

13. The non-resistive contact sensor assembly of claim 12, wherein the dry electrode component is adapted to avoid resistive contact with human skin.

14. The non-resistive contact sensor assembly of claim 1, wherein the casing is adapted to make direct resistive contact with a surface of the object of interest.

15. The non-resistive contact sensor assembly of claim 14, wherein the dry electrode component is adapted to avoid resistive contact with human skin.

16. The non-resistive contact sensor assembly of claim 1, wherein the assembly is in the form of a sensor head.

17. The non-resistive contact sensor assembly of claim 1, wherein the casing serves as a reference with regard to the electrical signal from the object of interest.

18. A non-resistive contact sensor assembly, comprising:
    a dry electrode component for receiving an electrical signal from an object of interest;
    a signal processing component for processing the electrical signal, wherein:
        the signal processing component includes an A/D converter that converts the electrical signal from the object of interest to a digitized signal, and
        the dry electrode component and signal processing component together define an electric field sensor device; and
    a casing in which the signal processing component is surrounded or embedded;
    wherein the casing is part of a housing for the assembly, and wherein the dry electrode component is exposed to the exterior of the housing;
    wherein the casing is electrically isolated from the dry electrode component; and
    wherein the casing is a conductive casing that acts as an electrical reference with regard to the electrical signal from the object of interest.

* * * * *